Figure 1:
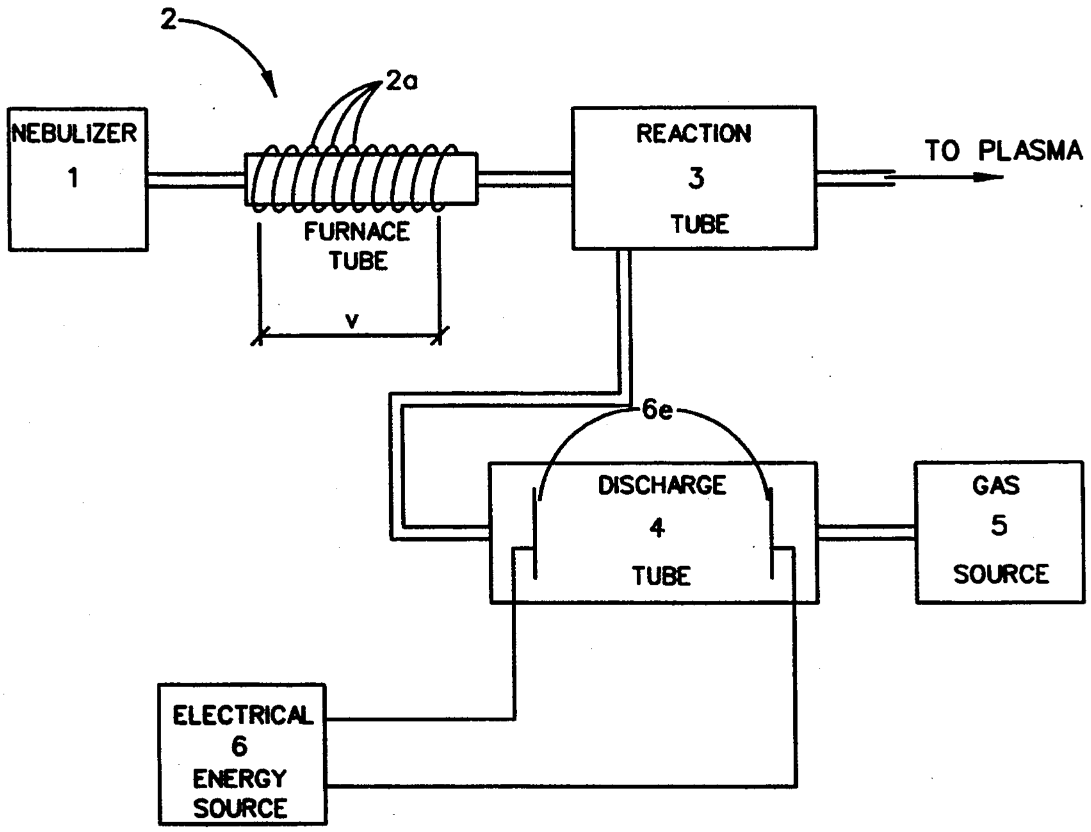

US005404219A

United States Patent [19]

D'Silva

[11] Patent Number: 5,404,219

[45] Date of Patent: Apr. 4, 1995

[54] SYSTEM FOR ENHANCING DETECTION OF SAMPLE COMPONENTS IN PLASMA BASED SAMPLE ANALYSIS SYSTEMS, AND METHOD OF USE

[75] Inventor: Arthur P. D'Silva, Ames, Iowa

[73] Assignee: Cetac Technologies Inc., Omaha, Nebr.

[21] Appl. No.: 177,256

[22] Filed: Jan. 4, 1994

[51] Int. Cl.[6] .......... G01J 3/30

[52] U.S. Cl. .......... 356/316

[58] Field of Search .......... 356/316, 36, 317; 315/111.21, 111.51; 219/121.54, 121.57

[56] References Cited

U.S. PATENT DOCUMENTS

| | | | |
|---|---|---|---|
| 3,916,034 | 10/1975 | Tsuchimoto | 427/38 |
| 4,378,499 | 3/1983 | Spangler et al. | 250/284 |
| 4,633,082 | 12/1986 | Sauers | 200/282 |
| 4,926,021 | 5/1990 | Streusand et al. | 219/121.59 |
| 5,089,746 | 2/1992 | Rosenblum et al. | 315/111.81 |
| 5,155,547 | 10/1992 | Casper et al. | 356/316 |

*Primary Examiner*—Vincent P. McGraw
*Assistant Examiner*—K. P. Hantis
*Attorney, Agent, or Firm*—James D. Welch

[57] ABSTRACT

A system and method for extending the limits of detection of plasma based sample analysis systems is disclosed. The preferred embodiment of the present invention system provides a reaction tube which is connected to both a furnace tube and a discharge tube. During use a nebulized sample is caused to pass through the furnace tube wherein its temperature is caused to become elevated. As well, a volatile atom containing, primarily molecular, gas is caused to flow through the discharge tube, while an energy providing electrical discharge occurs therein, such that dissociated volatile atoms are produced. The method of the present invention provides that typically elevated temperature nebulized sample, and the dissociated volatile atoms, be simultaneously entered into a reaction means wherein relatively easily dissociated molecules containing nebulized sample components are formed. The formed relatively easily dissociated molecules, being easier to dissociate than molecules present in the original nebulized sample, it should be appreciated effectively allow detection of nebulized sample components in a plasma based system utilizing the present invention, at lower concentration limits, compared to plasma analysis systems not utilizing the present invention.

8 Claims, 1 Drawing Sheet

SYSTEM FOR ENHANCING DETECTION OF SAMPLE COMPONENTS IN PLASMA BASED SAMPLE ANALYSIS SYSTEMS, AND METHOD OF USE

TECHNICAL FIELD

The present invention relates to plasma based sample analysis systems and methods of use, and more particularly to a system and method for creating easily dissociated volatile molecules of sample components, by interaction with, typically, dissociated hydrogen and/or fluorine atoms prior to plasma mediated analysis of said sample components.

BACKGROUND

The use of plasmas in the analysis of samples is well known. Generally, a sample in a nebulized form, is entered to a space inside a tube in which a plasma is caused to exist, and resulting emitted electromagnetic radiation is directed into a system for identifying the wavelength(s) present therein. Said present wavelength(s) are identifying of certain molecular and elemental contents of said sample.

A problem which can present during use of plasma based sample analysis systems is that some samples, even in highly nebulized form, (e.g. particles of thirteen (13) microns or less in diameter), can be difficult for plasmas to dissociate into component molecules and/or elemental atoms. This is often true, for instance, when sample is present in a molecular oxide form. Use of a higher energy plasma is, of course, one approach to overcoming the problem and can provide valuable results, particularly when it is desired to completely fragment the sample into elemental components. Another approach to the problem would be to expose nebulized sample to dissociated volatile atoms prior to entry thereof into a plasma, so that volatile, more easily dissociated, sample component containing molecules of are formed, (such as hydrides and/or fluorides), and injected into said plasma instead of originally present, more stable, sample component containing molecules.

A search for Patents which describe the use of volatile atoms to create volatile compounds with sample components prior to the entering thereof into a plasma indicates that little has been done in the area.

A Patent to Sauers, U.S. Pat. No. 4,633,082 is perhaps the most relevant reference discovered, but it describes a system for detecting breakdown of electrical equipment. This Patent states that sulfur-hexafluoride gas is often utilized as an insulator in high voltage systems. Electrical breakdown occurring in said high voltage systems causes formation fluorides of contaminants inside said high voltage equipments, which fluorides can be detected by, for instance, gas chromatography systems. Periodic sampling and analysis of the sulfur-hexafluoride insulating gas can thus provide early detection of electrical breakdown inside said electrical equipment.

Another Patent, U.S. Pat. No. 4,378,499 to Spanger et al. describes a system for detecting ion mobility. Selectivity and sensitivity are enhanced by converting through surface interactions sample gas or vapor to a form more readily ionized or by converting through surface interactions interferent gas or vapor to a form less readily ionized. Use of fluoride salts are mentioned as suitable for halogenating organophospherous compounds.

U.S. Pat. No. 5,089,746 to Rosenblum describes the use of fluorine in a feed gas dissociated in a plasma to react with a boron containing liner to form volatile species which more easily leave the surface thereof. The purpose is to facilitate provision of boron in a beam for use ion implantation.

A Patent to Strusand et al., describes the presence of a mixing chamber into which a sample of reactive gas or vapor is caused to flow, wherein it is mixed with a plasma gas including water vapor or solvent.

No known reference, however, teaches that a sample in a nebulized form should be caused to mix with volatile dissociated fluorine and/or hydrogen atoms, for instance, prior to entry into a plasma based sample analysis system plasma, to provide enhancement of the limit of detection of nebulized sample components. A need exists for such a system and method of use.

DISCLOSURE OF THE INVENTION

The present invention meets the need identified in the Background Section. The present invention provides that prior to injection into a plasma of a plasma based sample analysis system, a nebulized sample, (typically but not necessarily provided by an ultrasonic nebulizer), should be heated in a furnace tube, then mixed and reacted with, for instance, dissociated fluorine and/or hydrogen atoms in a reaction tube. Said dissociated hydrogen and/or fluorine atoms, for instance, typically being produced from fluorine and/or hydrogen containing molecules in a gas, by a preliminary electric discharge, in a discharge tube. In addition, the preferred embodiment provides that the reaction tube should be lined with a gettering material such as nickel or titanium. Said gettering material serves to absorb oxygen atoms released when sample hydrides or fluorides, for instance, are formed during reaction of sample present in an oxide form. This serves to prevent sample component recombination with said released oxygen atoms. Said lining also serves to absorb oxygen atoms entered from other sources, and prevents the reaction tube, (which is typically made of quartz), from being etched by fluorine atoms during use.

It should be understood in particular, that in general, fluorides and hydrides of sample components are more easily dissociated by a plasma than is the same sample component present in an oxide molecular form, for instance.

The present invention then provides that nebulized sample be mixed with volatile atoms so that relatively easily dissociated compounds containing sample components are formed. The purpose being to provide relatively easily dissociated volatile molecules to a plasma in a plasma based sample analysis system. A direct result thereof is an extension of the limits of detection as regards the presence of sample components originally present in relatively less easily dissociated molecular form.

SUMMARY OF THE INVENTION

Plasma based sample analysis systems have inherent limitations as regards sample component detection. That is, sample components present in relatively stable molecular form can, in certain instances, be difficult to dissociate from their containing molecules, and detect, using plasmas of reasonable energies. Use of relatively high plasma energies offers a known approach to accomplishing, with varying degrees of success, dissociation of stable sample component containing molecules. Another approach to attacking the identified problem, would be to free sample components from relatively difficult to dissociate molecules and cause formation of relatively more volatile, more easily dissociated, sample component containing molecules, prior to entry thereof into a plasma.

The present invention provides that prior to entry to a plasma, a sample in a nebulized form should be heated and then mixed with dissociated volatile atoms such as fluorine and/or hydrogen, for instance, in a reaction tube. The result of which being the formation of relatively more easily dissociated nebulized sample component fluoride and/or hydride molecules, for instance. Formation of said dissociated volatile fluorine and/or hydrogen atoms, for instance, typically being by application of electric energy to a gas which contains fluorine and/or hydrogen containing molecules, in a discharge tube, by means of a preliminary electric discharge.

The preferred embodiment of the present invention also provides that the inner surface of the reaction tube therein be lined with an oxygen gettering material such as nickel or titanium, for instance. The presence of said oxygen gettering material serves to minimize formation of typically relatively more stable, less easily dissociated, sample component oxide molecules in said reaction tube. The presence of a lining material, on the inner surface of a reaction tube made of quartz, also serves to prevent etching thereof by fluorine atoms during use.

It is therefore a purpose of the present invention to teach a system and method for increasing the limits of sample component detection achievable by plasma based sample analysis systems in a manner which does not require that plasma energy be unnecessarily increased.

It is a further purpose of the present invention to teach a system which, in its preferred embodiment, enhances achievable results by minimizing the effect of oxygen present in the reaction tube thereof, during use.

BRIEF DESCRIPTION OF THE DRAWINGS FIG. 1 shows the system of the present invention in a diagramatic from.

DETAILED DISCLOSURE

Turning now to the Drawings, there is shown in FIG. 1 a diagramatic representation of the system of the present invention. Shown are block representations of a nebulizer (1), a furnace tube (2), (shown with a resistive element (2*a*) coiled therearound), a reaction tube (3), a source (5) of, for instance, a fluorine and/or hydrogen atom containing gas, a discharge tube (4) and a source of electrical energy (6) with electrodes (6*e*) shown present at ends of said discharge tube (4).

During use a nebulized sample is provided by nebulizer (1) to furnace tube (2) wherein said nebulized sample is heated to between, typically, one-hundred (100) and eight-hundred (800) degrees centigrade. Said heated nebulized sample is then passed into reaction tube (3) wherein it is mixed with, for instance, dissociated fluorine and/or hydrogen atoms. Said dissociated fluorine and/or hydrogen, atoms being formed in discharge tube (4), when a gas containing said fluorine and/or hydrogen in a molecular form, is subjected to electrical energy provided by the source of electrical energy (6), during an electrode (6*e*) mediated electric discharge in said discharge tube (4).

Nebulized sample, and dissociated fluorine and/or hydrogen atoms, for instance, are then each passed into, and caused to be mixed with one another in reaction tube (3). The result being formation of relatively easily dissociated sample component fluorides and/or hydrides, for instance, depending on the contents of the gas provided by source (5) and of said nebulized sample. When sulfur-hexafluoride is provided to discharge tube (4), for instance, sample component fluorides can be formed in reaction tube (3) and when hydrogen gas is provided by source (5), sample component hydrides can be formed in said reaction tube (3).

It is to be understood that the method of the present invention is not limited to the case wherein fluorides and/or hydrides of sample components are formed, but rather can be practiced with any appropriate gas being provided by source (5), which appropriate gas serves to produce relatively easily dissociated sample component containing molecules formed in reaction tube (3), by reaction between nebulized sample provided from nebulizer (1) and dissociated atoms provided by discharge tube (4). It is, however, mentioned that formation of sample component fluorides is particularly applicable when nebulized sample components include U2O3, ThO2, and Ho2O3 for instance. Formation of sample component hydrides is particularly applicable when nebulized sample components include As, Se, and Pb for instance. As well, any means of heating nebulized sample can be utilized as can any means of providing dissociated volatile atoms. That is, the present invention is not limited to the use of resistive heating elements and/or electrical discharge respectively.

However, it is also to be understood that a source of electrical energy (6) will typically operate at fifteen (15 KV) kilovolts, fifty (50) watts and at a frequency of two-hundred (200 KHZ) kilohertz.

Also, while not a strict limitation, it is noted that a typical discharge tube has an inner diameter of approximately one (1) milimeter.

Continuing, in the preferred embodiment, the inner surface of the reaction tube (3) is lined with a material such as nickel or titanium. Other materials might also be used. The purpose of said lining being to, first, protect the reaction tube, (which is typically made of quartz), from being etched by fluorine atoms, for instance, during use; and second, to serve as a getter for oxygen atoms released from nebulized sample present in an oxide form, during interaction with dissociated fluorine and/or hydrogen atoms, for instance, in said reaction tube (3), as well as oxygen entered from any other source. Gettering of oxygen atoms present in reaction tube (3) during use prevents formation, or reformation, of nebulized sample component oxides therein. It is emphasized that nebulized sample component oxides are typically more difficult to dissociate in a plasma than are nebulized sample component fluorides and/or hydrides, for instance.

It is mentioned that the source (5) of gas containing, for instance, fluorine and/or hydrogen, can be a single tank, or can be multiple tanks. For instance, a tank containing sulfur-hexafluoride and/or hydrogen, and a tank containing a carrier gas such as argon and/or helium might both be fed to a mixing system placed prior to discharge tube (4) so that an intended mixture of said gasses results for entry into said discharge tube (4) during use. In the alternative, appropriate mixtures of gasses can be entered into single tanks prior to utilization in the present invention, thereby eliminating the need to carry out a mixing process during practice of the present invention. Ten (10%) percent mixtures of sulfur-hexafluoride and argon in single tanks, for instance, are standardly available.

It is also mentioned that neither sulfur or fluorine atoms interfere with detection of nebulized sample components which produce a spectra of electromagnetic radiation, when excited by a plasma in which they are present, with wavelengths between one-hundred-ninety (190) and one-thousand (1000) nanometers. As a result sulfur-hexafluoride is particularly well suited for use in the present invention.

Finally, the terms "furnace tube", "Discharge tube" and "Reaction tube" were used in the foregoing to aid description of the preferred embodiments of the various components of the present invention system. Said terms are identifying of an example of a means for performing functions associated therewith. It is to be understood that any means which perform equivalent functions are to be considered equivalent and within the scope of the claims.

Having hereby disclosed the subject matter of the present invention, it should be obvious that many modifications, substitutions, and variations of the present invention are possible in light of the teachings. It is therefore to be understood that the invention can be practiced other than as specifically described, and should be limited in breadth and scope only by the claims.

I claim:

1. A system for enhancing the limits of detection of plasma based sample analysis systems comprising:

a furnace tube;

a discharge tube; and a reaction tube;

said furnace and discharge tubes both being attached to said reaction tube; such that during use a nebulized sample is caused to enter said reaction tube after passing through said furnace tube wherein the temperature of said nebulized sample is caused to be elevated; and such that during use a gas containing volatile atoms, primarily in molecular form, is caused to enter said discharge tube while energy is provided thereto, thereby causing volatile atoms to be present in a dissociated form, which dissociated volatile atoms are caused to enter said reaction tube simultaneously with said elevated temperature nebulized sample such that mixing of, and reaction between, said dissociated volatile atoms and said nebulized sample occurs; the result being formation of sample component containing volatile molecules which are relatively more easily dissociated than molecules originally present in said nebulized sample;

the purpose being to produce relatively more easily dissociated sample component containing volatile molecules for entry into the plasma of the plasma based sample analysis system;

the end effect being that the sample component detection limits of said plasma based sample analysis system are extended.

2. A system for enhancing the limits of detection as in claim 1, in which the gas containing volatile atoms contains sulfur-hexafluoride such that the relatively more easily dissociated sample component containing molecules formed are relatively fluorides of said sample components.

3. A system for enhancing the limits of detection as in claim 1, in which the gas containing volatile atoms contains hydrogen such that the relatively more easily dissociated sample component containing molecules formed are hydrides of said sample components.

4. A system for enhancing the limits of detection as in claim 1, in which the means for raising the temperature of the nebulized sample comprises resistive heating means.

5. A system for enhancing the limits of detection as in claim 1, in which the means for providing energy to the discharge tube comprises a system for producing an electric discharge.

6. A method of enhancing the limits of detection of a plasma based sample analysis system comprising the steps of:

a. obtaining a system for enhancing the limits of detection of plasma based sample analysis systems comprising:

a furnace tube;

a discharge tube; and a reaction tube;

said furnace and discharge tubes both being attached to said reaction tube; such that during use a nebulized sample is caused to enter said reaction tube after passing through said furnace tube wherein the temperature of said nebulized sample is caused to be elevated; and such that during use a gas containing volatile atoms, primarily in molecular form, is caused to enter said discharge tube while energy is provided thereto, thereby causing volatile atoms to be present in a dissociated form, which dissociated volatile atoms are caused to enter said reaction tube simultaneously with said elevated temperature nebulized sample such that mixing of, and reaction between, said dissociated volatile atoms and said nebulized sample occurs; the result being formation of sample component containing volatile molecules which are relatively more easily dissociated than molecules originally present in said nebulized sample;

the purpose being to produce relatively more easily dissociated sample component containing volatile molecules for entry into the plasma of the plasma based sample analysis system;

the end effect being that the sample component detection limits of said plasma based sample analysis system are extended;

b. entering volatile atom containing gas to said discharge tube and entering energy thereto such that dissociated volatile atoms are formed;

c. simultaneously causing said nebulized sample and said volatile dissociated atoms to enter, mix and react in said reaction tube such that relatively more easily dissociated sample component containing molecules are caused to form;

e. causing said relatively more easily dissociated sample component containing molecules to enter the plasma of a plasma based sample analysis system and detecting and analyzing the resulting electromagnetic radiation to identify said sample components present.

7. A system for enhancing the limits of detection of plasma based sample analysis systems comprising:

a furnace means;

a discharge means; and a reaction means;

said furnace and discharge means both being attached to said reaction means; such that during use a nebulized sample is caused to enter said reaction means after passing through said furnace means wherein the temperature of said nebulized sample is caused to be elevated; and such that during use a gas containing volatile atoms, primarily in molecular form, is caused to enter said discharge means while energy is provided thereto, thereby causing volatile atoms to be present in a dissociated form, which dissociated volatile atoms are caused to enter said reaction means simultaneously with said elevated temperature nebulized sample such that mixing of, and reaction between, said dissociated volatile atoms and said nebulized sample occurs; the result being formation of sample component containing volatile molecules which are relatively more easily dissociated than molecules originally present in said nebulized sample;

the purpose being to produce relatively more easily dissociated sample component containing volatile molecules for entry into the plasma of the plasma based sample analysis system;

the end effect being that the sample component detection limits said plasma based sample analysis system are extended.

8. A method of enhancing the limits of detection of a plasma based sample analysis system comprising the steps of:

a. obtaining a system for enhancing the limits of detection of plasma based sample analysis systems which provides means for causing dissociated volatile atoms to be present in a dissociated form, which dissociated volatile atoms are caused to enter a reaction means simultaneously with nebulized sample such that mixing of, and reaction between, said dissociated volatile atoms and said nebulized sample occurs; the result being formation of sample component containing volatile molecules which are relatively more easily dissociated than molecules originally present in said nebulized sample;

the purpose being to produce relatively more easily dissociated sample component containing volatile molecules for entry into the plasma of the plasma based sample analysis system;

the end effect being that the sample component detection limits of said plasma based sample analysis system are extended.

b. entering dissociated volatile atoms thereto;

c. simultaneously entering nebulized sample thereto so that said dissociated volatile atoms and nebulized sample, mix and react in said reaction means such that relatively more easily dissociated sample component containing molecules are caused to form;

e. causing said relatively more easily dissociated sample component containing molecules to enter the plasma of a plasma based sample analysis system and detecting and analyzing the resulting electromagnetic radiation to identify said sample components present.

* * * * *